(12) United States Patent
Bacon et al.

(10) Patent No.: US 9,592,160 B2
(45) Date of Patent: Mar. 14, 2017

(54) WOUND CARE BANDAGE AND METHOD OF WOUND HEALING

(71) Applicant: Garwood Medical Devices, LLC, Buffalo, NY (US)

(72) Inventors: Wayne Bacon, Buffalo, NY (US); Gregg Gellman, Getzville, NY (US)

(73) Assignee: Garwood Medical Devices, LLC, Buffalo, NY (US)

( * ) Notice: Subject to any disclaimer, the term of this patent is extended or adjusted under 35 U.S.C. 154(b) by 0 days.

(21) Appl. No.: 14/854,696

(22) Filed: Sep. 15, 2015

(65) Prior Publication Data

US 2016/0213521 A1    Jul. 28, 2016

Related U.S. Application Data

(60) Provisional application No. 62/050,795, filed on Sep. 16, 2014.

(51) Int. Cl.

| A61F 13/00 | (2006.01) |
|---|---|
| A61N 1/04 | (2006.01) |
| A61F 13/02 | (2006.01) |
| A61F 15/00 | (2006.01) |

(52) U.S. Cl.
CPC ...... *A61F 13/00063* (2013.01); *A61F 13/025* (2013.01); *A61F 13/0206* (2013.01); *A61F 13/0243* (2013.01); *A61F 13/0256* (2013.01); *A61F 15/00* (2013.01); *A61N 1/0468* (2013.01); *A61N 1/0492* (2013.01)

(58) Field of Classification Search
CPC .......... A61F 13/00063; A61F 13/0243; A61F 13/0206; A61F 13/025; A61N 1/04
USPC ....................................... 607/149, 152, 148
See application file for complete search history.

(56) References Cited

U.S. PATENT DOCUMENTS

| 4,556,051 | A | 12/1985 | Maurer |
|---|---|---|---|
| 4,635,641 | A | 1/1987 | Hoffman |
| 4,982,742 | A | 1/1991 | Claude |
| 5,395,398 | A | 3/1995 | Rogozinski |
| 5,423,874 | A * | 6/1995 | D'Alerta ............ A61N 1/36021 607/46 |
| 6,438,428 | B1 * | 8/2002 | Axelgaard ........... A61N 1/0452 607/148 |

(Continued)

FOREIGN PATENT DOCUMENTS

WO    WO 2015/168720    11/2015

*Primary Examiner* — Kim M Lewis
(74) *Attorney, Agent, or Firm* — Del Vecchio and Stadler LLP

(57) ABSTRACT

A wound healing system and a wound care bandage are provided. The wound care bandage has an electronics housing that houses a battery and wound care microcontroller. A bandage layer is provided and it defines a pad recess in which a pad is disposed. The pad has channels to allow for airflow. The wound care bandage at least first and second snap button electrodes, but there may be more snap button electrodes in other preferred embodiments. There are also electrically conductive adhesive strips with one being in contact with each of the first and second snap button electrodes. When current is controllably supplied to the first and second snap button electrodes a plurality of electric current flow paths are generated and that extend across the wound and stimulate the healing of the wound. The wound care bandage can be monitored and controlled wirelessly.

17 Claims, 14 Drawing Sheets

(56) References Cited

U.S. PATENT DOCUMENTS

| | | |
|---|---|---|
| 6,535,767 B1 | 3/2003 | Kronberg |
| 7,390,214 B2 | 6/2008 | Tsiang |
| D579,989 S | 11/2008 | Bingham, Jr. et al. |
| 7,668,580 B2 | 2/2010 | Shin et al. |
| 7,756,586 B2 * | 7/2010 | Wenzel .................. A61N 1/326 607/50 |
| 8,086,318 B2 | 12/2011 | Strother |
| 8,093,444 B2 | 1/2012 | Flick |
| 8,821,176 B2 | 9/2014 | Egloff et al. |
| 8,900,217 B2 | 12/2014 | Malhi |
| 8,958,883 B2 | 2/2015 | Mueller et al. |
| 9,174,042 B2 * | 11/2015 | Schonenberger .... A61N 1/0428 |
| 2002/0019652 A1 * | 2/2002 | Da Silva .............. A61N 1/0456 607/72 |
| 2004/0044384 A1 | 3/2004 | Leber et al. |
| 2004/0254624 A1 | 12/2004 | Johnson |
| 2008/0188779 A1 | 8/2008 | Vallero |
| 2009/0216294 A1 | 8/2009 | Ewing et al. |
| 2013/0046362 A1 | 2/2013 | Colhurst |
| 2013/0158425 A1 | 6/2013 | Kaye et al. |
| 2015/0099976 A1 | 4/2015 | Ghaffari et al. |
| 2015/0151124 A1 | 6/2015 | Marshall et al. |
| 2015/0190074 A1 | 7/2015 | McRae |
| 2015/0200488 A1 | 7/2015 | Egloff et al. |
| 2015/0305974 A1 | 10/2015 | Ehrenreich et al. |
| 2016/0022989 A1 | 1/2016 | Pfeifer |
| 2016/0058380 A1 | 3/2016 | Lee et al. |
| 2016/0101284 A1 | 4/2016 | Bachinski et al. |
| 2016/0129248 A1 | 5/2016 | Creasey et al. |

* cited by examiner

Section A-A

Section B-B

WOUND CARE BANDAGE AND METHOD OF WOUND HEALING

CROSS REFERENCE TO RELATED APPLICATION

This application claims priority to U.S. Provisional Application having Ser. No. 62/050,795 filed on Sep. 16, 2014 the entire disclosure of which is hereby incorporated herein by reference.

TECHNICAL FIELD OF INVENTION

This invention is directed to patients having wounds and accelerating the healing process of the wound with a wound care bandage.

BACKGROUND OF INVENTION

When a person suffers an injury or has surgery resulting in a wound it is critical that the wound be closed and heals as quickly as possible. Such rapid wound healing will, among other things, increase patient comfort, decrease the risk of the wound re-opening, decrease the risk of re-injuring the wound site, and decrease the length of a hospital stay and decrease scarring.

Of course, healing wounds has long been problematic for a plurality of reasons. For example, some wounds are difficult to heal because of the physical condition of the patient or the nature of the wound. In addition, some wounds simply refuse to heal even when the patient is under the care of skilled health care professionals. Other wounds are such that antibiotics, negative pressure therapy, and wet therapy have no impact on actually healing the wound.

There are several techniques for healing wounds that make use of electrical currents that flow across the wound, and there are three types of electrically assisted treatments:

- high-volt pulsed current (hereinafter referred to herein as HVPC);
- low-voltage monophasic-pulsed current; (hereinafter referred to herein as LVMPC); and,
- low-voltage biphasic-pulsed current (hereinafter referred to herein as LVBPC).

However, the current methods for using any of the electronic methods require a variety of different pieces of equipment and often require the patient to remain tethered to equipment with cords leading from the patient to the equipment. Additionally, separate bandages are required to ensure the wound is protected and any fluids are captured. In addition, patients that are not already restricted in bed typically will not follow through with its use of these treatment devices and thus the self-efficacy ratings for these devices are low.

In addition, these devices are not widely used because it also requires a lot of set-up time to put these devices in place. These devices must be set-up next to the patients and the cords that are associated with these devices have to properly routed by medical providers, all of which takes time and expense. Electrodes used in the treatments are also very difficult to place properly, and improper placement of the electrodes will oftentimes result in ineffective medical treatment.

What is needed is a new and improved way to treat wounds such that they heal faster while at the same time the amount of equipment required for the treatment is small and easy to use and eliminates or reduces the problems associated with the devices currently in use. A device is needed that is small and allows for patient mobility and allows for facilitated patient transport.

SUMMARY OF THE INVENTION

This invention is directed to a system for wound healing that includes a wound care bandage that also provides for wound treatment. The wound care bandage has a bandage layer in which a pad is disposed for absorbing bodily fluids, and has at least two snap button electrodes. The snap button electrodes provide current that passes across the wound of the patient to accelerate healing of the wound. Not only does the wound care bandage ensure the comfort of the patient, but the wound care bandage also allows for improved patient freedoms as well as simplifying the administration of the treatment by trained personnel and heath care providers.

BRIEF DESCRIPTION OF THE DRAWING FIGURES

DETAILED DESCRIPTION OF THE INVENTION

Figure 1:
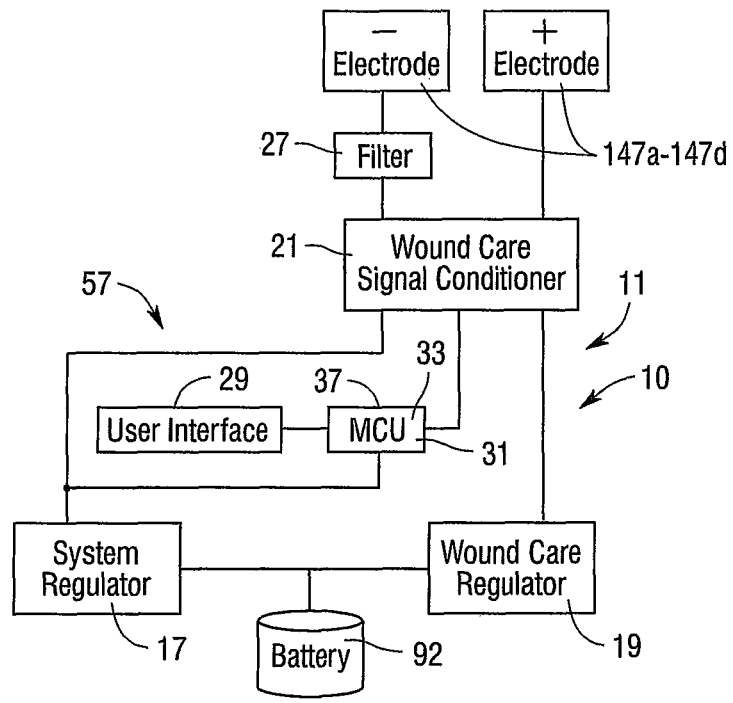
FIG. 1 is a schematic of a wound care system for enhancing and accelerating the healing process of a wound.
Figure 5:
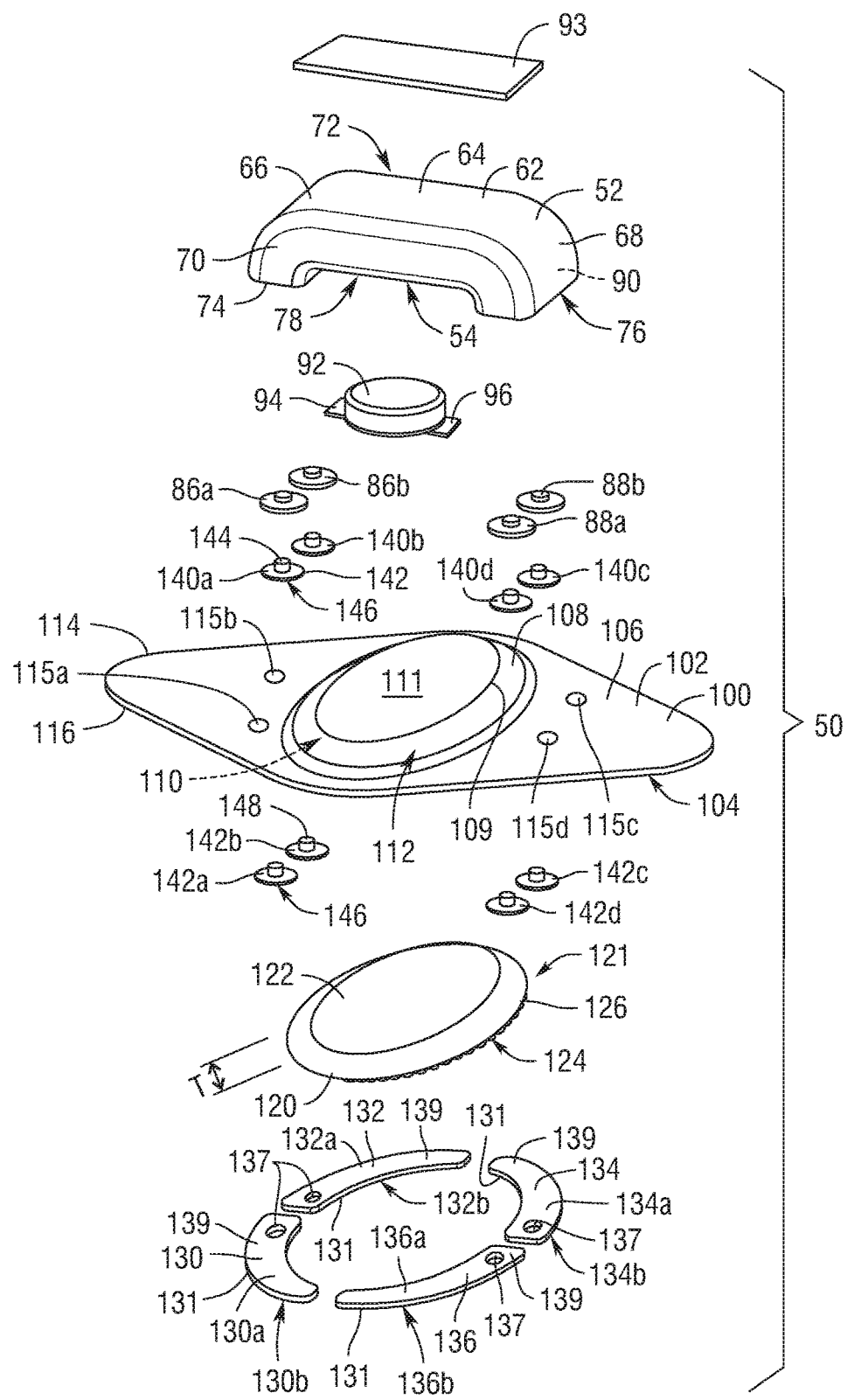
FIG. 5 is an exploded view of a wound care bandage.

As shown in FIGS. 1 and 5, there is a wound healing system 10. The wound healing system includes a battery 92, and wound care bandage electronics 93 that include a system regulator 17, a wound care regulator 19, a wound care signal conditioner 21, snap button electrodes 147a, 147b, 147c and 147d, a filter 27, a user interface 29 and a programmed wound care microcontroller 31 (hereinafter referred to as wound care MCU 31).

Figure 2:
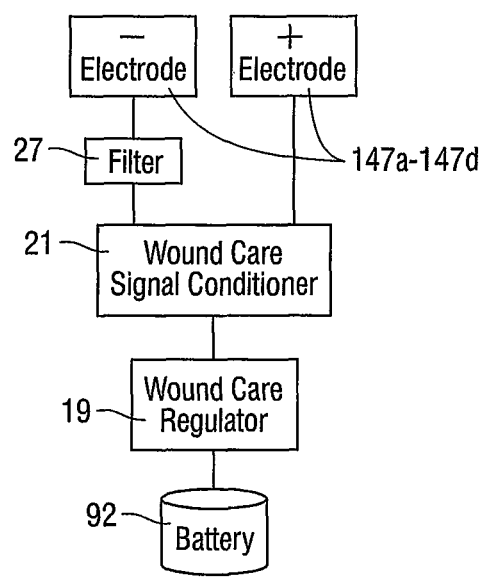
FIG. 2 is a portion of the schematic of FIG. 1.
Figure 3:
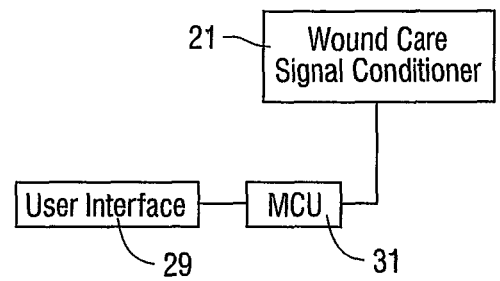
FIG. 3 is another portion of the schematic of FIG. 1.
Figure 4:
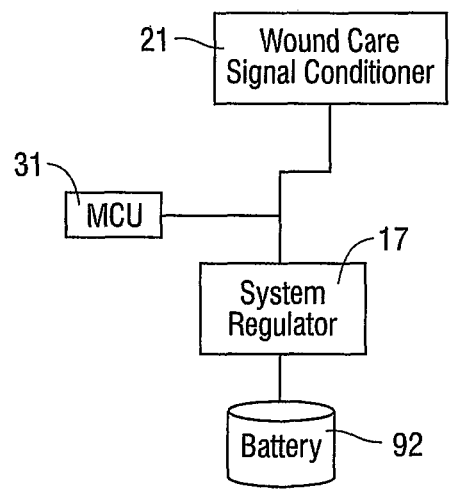
FIG. 4 is another portion of the schematic of FIG. 1.

FIGS. 2-4 provide a more detailed breakdown of FIG. 1. FIG. 2 details the main power path wherein the battery 92 powers the wound care regulator 19 and powers the wound care signal conditioner 21. FIG. 3 details the control lines from the user interface 29 to the wound care MCU 31 to the wound care signal conditioner 21. As shown in FIG. 4 the battery 92 powers the system regulator 17 and powers the wound care MCU 31. The filter 27 shown in FIG. 1 is for oscillating current and for preventing undesirable low frequencies to pass, and the filter 27 connects to the snap button electrodes 147a-147d. For example, 1 kHz will be filtered out by the filter 27 as will be DC current. FIGS. 1-4 and associated wound care bandage electronics 93 will be described in greater detail presently.

Figure 6:
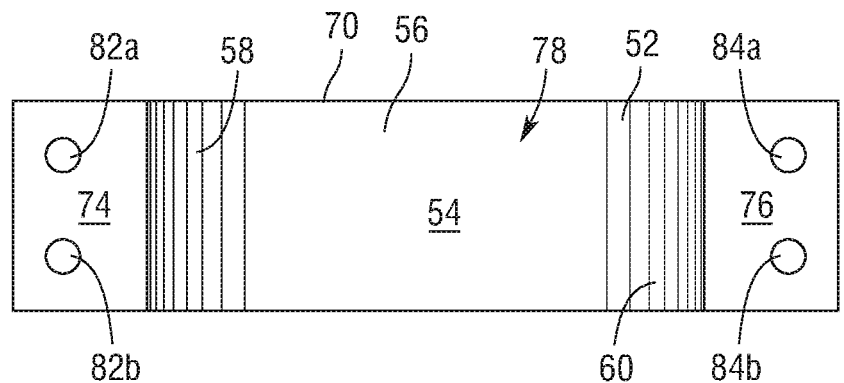
FIG. 6 is a bottom plan view of an electronics housing.
Figure 7:
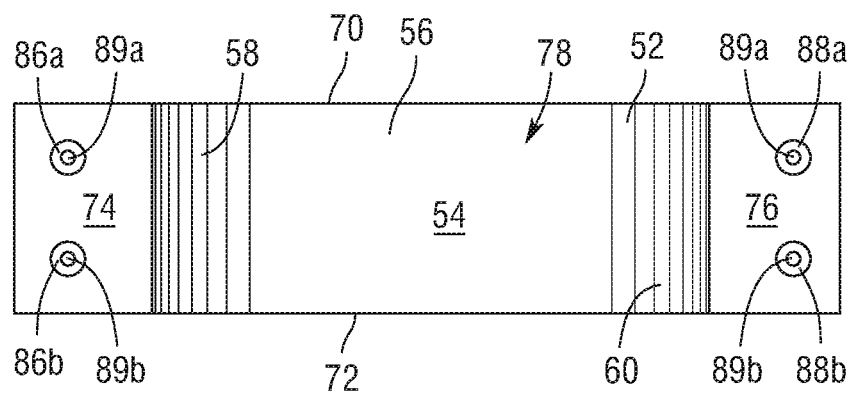
FIG. 7 is another bottom plan view of the electronics housing.
Figure 12:
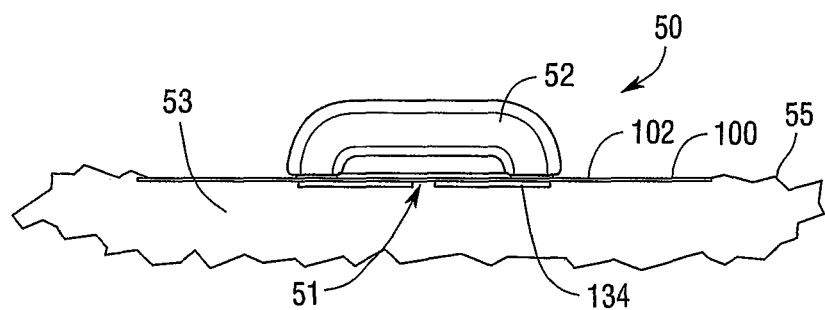
FIG. 12 is a front view of the wound care bandage when secured to the skin of a patient and disposed over a wound.

FIG. 5 is an exploded view of a wound care bandage 50. As will be described presently, the wound care bandage 50 causes electrical current to flow from electrodes and through a wound 51 of a patient 53 (see FIG. 12) to accelerate the healing of the wound 51. For ease of reference, a wound 51, a patient 53 and skin 55 are shown in FIG. 12. Returning now to FIG. 5, the wound care bandage 50 has an electronics housing 52 that has an inner side 54 (best shown in FIGS. 6 and 7) that includes a flat inner side portion 56 that extends to first and second concave side portions 58, 60, and has an opposed outer side 62 (shown in FIGS. 5 and 8-9) that has an outer side flat portion 64 that extends to first and second convex side portions 66, 68. The side flat portion 64 serves as a removable cover or lid that is held to the electronics housing 52 with for example a friction fit, such that it can be removed and attached to the electronics housing 52. The electronics housing 52 defines a hollow interior 90 that is accessible when the outer side flat portion 64 is removed. The electronics housing 52 also has opposed first and second sides 70, 72, (FIG. 5) each of which extends from the outer side 62 to the inner side 54. As shown in FIGS. 6 and 7, the electronics housing 52 has a first and second end walls 74, 76, and each of them extends to the inner and outer sides 54, 62, and each of them extends to the first and second sides 70, 72. The first and second end walls 74, 76 are co-planar and are rectangular shaped, but may be otherwise shaped in other preferred embodiments. The inner side 54 of the electronics housing 52 is concave shaped and the inner side 54 thus defines a bandage component recess 78 such that the electronics housing 52 can be positioned over a bandage layer 100 as will be described presently. The electronics housing 52 may be made of plastics, metals, fabrics and combinations thereof.

As shown in FIG. 6, the first end wall 74 defines a first pair of end wall openings 82a, 82b, and second end wall 76 defines a second pair of end wall openings 84a, 84b, respectively. As shown in FIG. 7, first and second conductive female snap components 86a, 86b are positioned in the first pair of end wall openings 82a, 82b and mounted to the first end wall 74. Third and fourth conductive female snap components 88a, 88b are positioned in the second pair of end wall openings 84a, 88b and mounted to the second end wall 76. All of the female snap components are structurally identical. Each of the first, second, third and fourth female snap components 86a, 86b, 88a, 88b defines a female snap recess commonly designated 89a, and each of the first, second, third and fourth female snap components 86a, 86b, 88a, 88b is made of metal or other electrically conductive material.

As previously mentioned, the electronics housing 52 defines a hollow interior 90 and disposed in the hollow interior is a battery 92 and the wound care bandage electronics 93 that are powered by the battery 92. In addition, first and second battery leads 94, 96 are connected to and extend from the battery 92. In one of the preferred embodiments the battery 92 is a 1.2 volt coin cell battery, and the battery 92 may be a embodied as a lithium coin cell battery or other suitable battery. The first battery lead 94 is wired to the wound care bandage electronics 93 and the second battery lead 96 is wired to the wound care bandage electronics 93 with wires commonly designated 97. The wound care bandage electronics 93, in turn, is wired to the first and second conductive female snap components 86a, 86b, and wired to the third and fourth conductive female snap components 88a, 88b with wires 97, such that electrical charges can be delivered to the first, second, third and fourth female conducive snaps.

Figure 8:
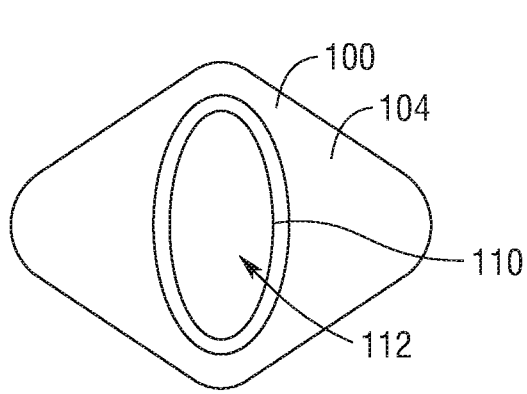
FIG. 8 is a bottom view of the bandage layer.
Figure 8A:
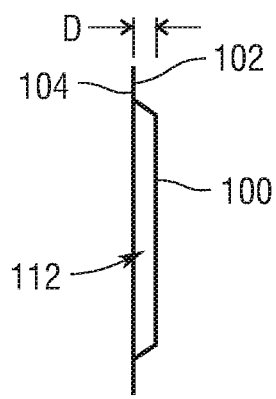
FIG. 8A is a side view of the bandage layer.

The wound care bandage 50 also has a bandage layer 100 that has opposed first and second bandage layer surfaces 102, 104. The first bandage layer surface 102 has a flat portion 106 that extends to a protruding portion 108 having a protruding portion end wall 111, such that protruding portion 108 is elevated relative to the flat portion 106 of the first bandage layer surface 102. The protruding portion has an elliptical shape 109 in one of the preferred embodiments, but may be differently shaped in other preferred embodiments. In one of the preferred embodiments the protruding portion end wall 111 is absent, and thus there is an opening defined by the protruding portion 108. A bottom plan view of the bandage layer 100 is shown in FIG. 8. As shown in FIG. 8, extending into the second bandage layer surface 104 is a bandage layer recessed portion 110 that defines a bandage layer recess 112, such that the existence of the protruding portion 108 results in the bandage layer recess 112 being formed in the bandage layer 100. As a result, the protruding portion 108 is hollow. As shown, the bandage layer recess 112 is elliptical shaped, but may be otherwise shaped in other preferred embodiments. The depth of the bandage layer recess 112 is designated D in FIG. 8A. The bandage layer 100 also defines first, second, third and fourth bandage layer snap openings 115a, 115b, 115c and 115d. The bandage layer 100 is made of an antimicrobial material in one of the preferred embodiments and can be made of fabrics, breathable fabrics, and other suitable materials including the following: a flexible adhesive backed material that is capable of conforming the body of the patient, a flexible adhesive backed material for carrying the conductive strips. The bandage layer 100 has a periphery 114 that has a trapezoidal shape 116, but the periphery 114 may be otherwise shaped in other preferred embodiments, for example the bandage layer 100 may have a periphery 114 that is circular-shaped, triangular shaped or any shape that is needed or desired for a particular application.

Figure 11:
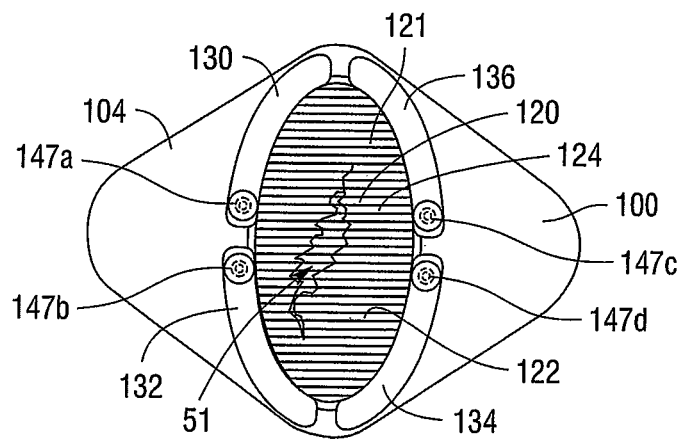
FIG. 11 is a bottom plan view of the wound care bandage with a wound shown for illustrative purposes.

As shown in FIGS. 5 and 11, the wound care bandage 50 also includes a pad 120 that has opposed first and second pad sides 122, 124. The first pad side 122 may be embodied such that it is flat. The pad 120 has an elliptical shape 121 that matches the shape of the bandage layer recess 112, and the pad 120 has a thickness designated T that is the same or substantially the same as a depth, designated D in FIG. 8A, of the bandage layer recess 112. The pad 120 is positioned in the bandage layer recess 112 defined by the bandage layer recessed portion 110. A friction fit or an adhesive may be used to hold the pad 120 in the bandage layer recess 112. When the pad 120 is disposed in the bandage layer recess 112 the second pad side 124 is flush with or may extend beyond the second bandage layer surface 104 such that the pad 120 will contact or will be proximal the wound 51. The second pad side 124 defines aeration channels 122 to allow for airflow between the second pad side 124 and the wound 51 in order to promote healing. The pad 120 is impregnated with antibacterial materials 126 in one of the preferred embodiments, for example silver particles and other antibacterial materials known to those having ordinary skill in the art. In another preferred embodiment the pad 120 is made of a highly absorbent breathable material, and may be treated with an antimicrobial solution.

The wound care bandage 50 also has first, second, third and fourth electrically conductive adhesive strips 130, 132, 134 and 136, respectively, for delivering current through the skin 55 of the patient 53 to the wound 51, and they are identically shaped in one of the preferred embodiments. As shown, the first, second, third and fourth electrically conductive adhesive strips 130, 132, 134 and 136 are arch-shaped 139, but it is to be understood that the shape of the first, second, third and fourth electrically conductive adhesive strips 130, 132, 134 and 136 may be otherwise embodied, for example they may be rectangular shaped or have virtually any geometry required for a particular application of wound treatment, and there may be more or less than four—electrically conductive adhesive strips present, again the number of electrically conductive strips can be varied to accommodate different applications and treatment of different wounds. All of these embodiments are intended to come within the scope of claims presented herein.

The first electrically conductive adhesive strip 130 has opposed first and second strip sides 130a, 130b and each side is coated in adhesive 131 that is conductive. The second electrically conductive adhesive strip 132 has opposed first and second strip sides 132a, 132b and each side is coated in an adhesive 131. The third electrically conductive adhesive strip 134 has opposed first and second strip sides 134a, 134b and each side is coated in adhesive 131. The fourth electrically conductive adhesive strip 136 has opposed first and second strip sides 136a, 136b and each side is coated in adhesive 131. The adhesive 131 is electrically conductive and the first, second, third and fourth electrically conductive adhesive strips 130, 132, 134 and 136 are electrically conductive. Each of the conductive first, second, third and fourth electrically conductive adhesive strips 130, 132, 134 and 136 also defines a strip opening commonly designated 137. Each of the conductive first, second, third and fourth electrically conductive adhesive strips 130, 132, 134 and 136 has a first strip side 130a, 132a, 134a and 136a, respectively, and an opposed second strip side 130b, 132b, 134b and 136b, respectively.

As shown in FIG. 5, the wound care bandage 50 also includes first, second, third and fourth conductive central snap components 140a, 140b, 140c, 140d that are identical and made of conductive metal or other conductive material, and each has a support portion 142 from which male member 144 extends, and wherein the male member 144 defines a female recess 146 (reference numbers 142, 144 and 146 only shown once in FIG. 5 for the sake of clarity). The support portion 142 has a circular shape in one of the preferred embodiments.

There are also first, second, third and fourth conductive base male snap components 142a, 142b, 142c and 142d that are identical and made of conductive metal or other conductive material, and each having a base male portion 146 from which a base male member 148 extends (reference numbers 146 and 148 only shown once in FIG. 5 for the sake of clarity). The base male portion 146 has a circular shape in one of the preferred embodiments.

Wound Care Bandage Assembly

Figure 9:
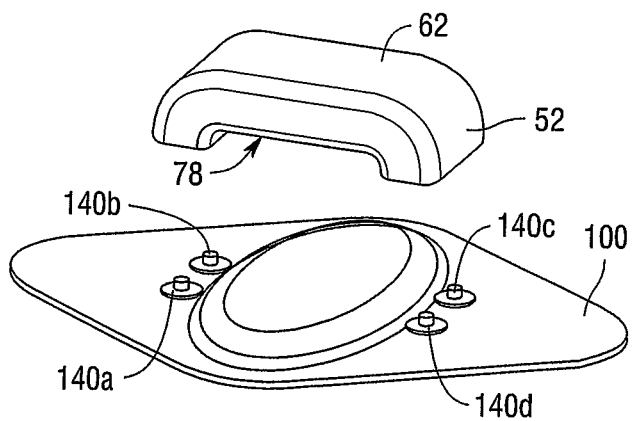
FIG. 9 is a perspective view of the electronics housing and a bandage layer prior to assembly.
Figure 10:
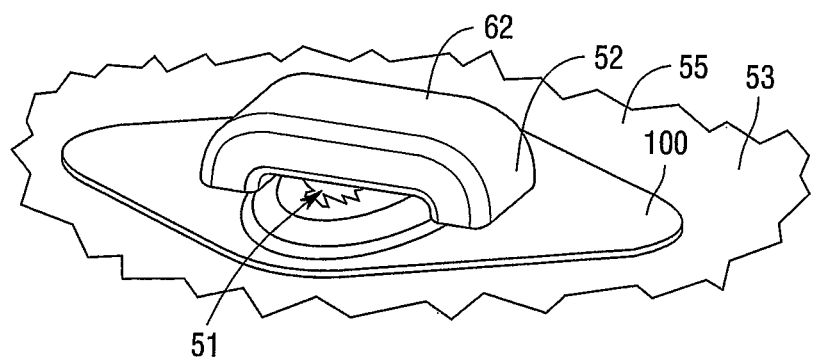
FIG. 10 is a perspective view of the wound care bandage when assembled and positioned over the wound of a patient.

Reference is now made to FIGS. 9-11. To assembly the wound care bandage 50, the electronics housing 52 is positioned above the bandage layer 100 such that the first and second conductive female snap components 86a, 86b are disposed over the first and second of snap openings 115a, 115b defined in the bandage layer 100, and the third and fourth conductive female snap components 88a, 88b are disposed over the third and fourth snap openings 115c, 115d defined in the bandage layer 100.

The base male members 148 of the first and second conductive base male snap components 142a, 142b are moved through the strip openings 137 defined in the first and second electrically conductive adhesive strips 130, 132, respectively, and through the first and second snap openings 115a, 115b defined in the bandage layer 100. Similarly, the base male member components 148 of the third and fourth conductive base male snap components 142c, 142d are moved through the strip openings 137 defined in the third and fourth electrically conductive strips 132, 136, respectively, and through the third and fourth snap openings 115c, 115d, respectively, defined in the bandage layer 100. At the same time the first strip sides 130a, 132a, 134a and 136a of the first, second, third and fourth electrically conductive adhesive strips 130, 132, 134 and 136 are brought into contact with and adhered to the second bandage layer surface 104 of the bandage layer 100.

Then, the female recesses 146 defined in the first and second of conductive central snap components 140a, 140b aligned with and are moved onto the base male members 148 of the first and second conductive base male snap components 142a, 142b, respectively. Once the first and second base male snap components 142a, 142b are received in the female recesses 146 of the first and second of conductive central snap components 140a, 140b they are held or snapped together. After snapping is completed, the bandage layer 100 is captured between and secured to the first and second of conductive central snap components 140a, 140b and the first and second base male snap components 142a, 142b, respectively.

Similarly, the female recesses 146 defined in the third and fourth conductive central snap components 140c, 140d are aligned with and are moved onto the base male members 148 of the third and fourth conductive base male snap components 142c, 142d, respectively. Once the second and third base male snap components 142c, 142d are received in the female recesses 146 of the third and fourth conductive central snap components 140c, 140d they are held or snapped together. After snapping is completed, the bandage layer 100 is captured between and secured to the third and fourth conductive central snap components 140c, 140d, respectively, and the first and second base male snap components 142c, 142d, respectively.

To complete the assembly of the wound care bandage 50 the male members 144 of the first and second conductive central snap components 140a, 140b are moved into or snapped into the first and second conductive female snap components 86a, 86b. Similarly, the male members 144 of the third and fourth conductive central snap components 140c, 140d, respectively, are moved into or snapped into the third and fourth conductive female snaps 88a, 88b.

As shown in FIG. 11, after snapping is completed, the snapped together first female snap component 86a, the first conductive central snap component 140a, and the first conductive base male component 142a form a first snap button electrode 147a, and the snapped together second female snap component 86b, the second conductive central snap component 140b, and the second conductive base male component 142b form a second snap button electrode 147b, and the third female snap component 88a, the third conductive central snap component 140c, and the third conductive base male component 142c form a third snap button electrode 147c, and the fourth female snap component 88b, the fourth conductive central snap component 140d, and the fourth conductive base male component 142d form a fourth snap button electrode 147d. The first, second, third and fourth snap button electrodes 147a, 147b, 147c and 147d, respectively, are capable of delivering electrical charges to the wound 51 though the skin 55 of the patient 55. The first snap button electrode 147a is also capable of delivering electrical charge to the first electrically conductive adhesive strip 130, the second snap button electrode 147b is also capable of delivering electrical charge to the second electrically conductive adhesive strip 132, the third snap button electrode 147c is also capable of delivering electrical charge to the third electrically conductive adhesive strip 134, and the fourth snap button electrode 147c is also capable of delivering electrical charge to the fourth electrically conductive adhesive strip 136. Thus, each of the first, second, third and fourth snap button electrodes 147a, 147b, 147c and 147d serves as an electrode that allow for multiple electrical signals to pass through a single snap connection.

It is pointed out that although the drawing figures show the first, second, third and fourth snap button electrodes 147a, 147b, 147c and 147d arranged in a rectangular shape with each electrode forming a corner thereof, in other preferred embodiments the shape formed by these electrodes form can be varied. For example, the first, second, third and fourth snap button electrodes 147a, 147b, 147c and 147d may be arranged to form the shape of virtually any quadrilateral, that is, each electrode forms a corner of the quadrilateral by modifying the shape of the electronics housing 52 or the end wall openings defined in the electronics housing 52.

Figure 13:
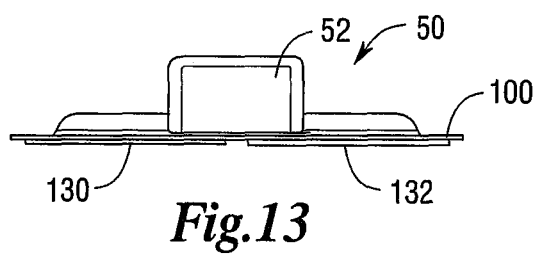
FIG. 13 is a left side view the wound care bandage.
Figure 14:
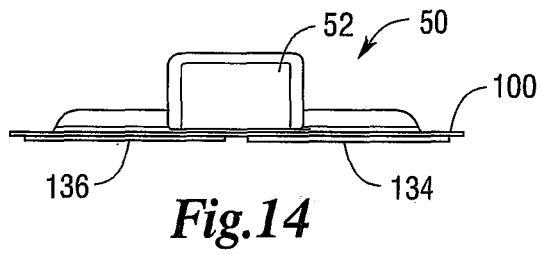
FIG. 14 is a right side view of the wound care bandage.
Figure 15:
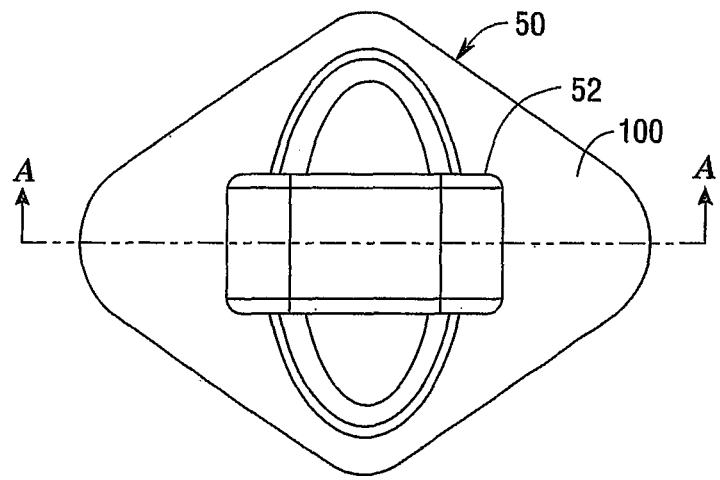
FIG. 15 is a top view of the wound care bandage.
Figure 16:
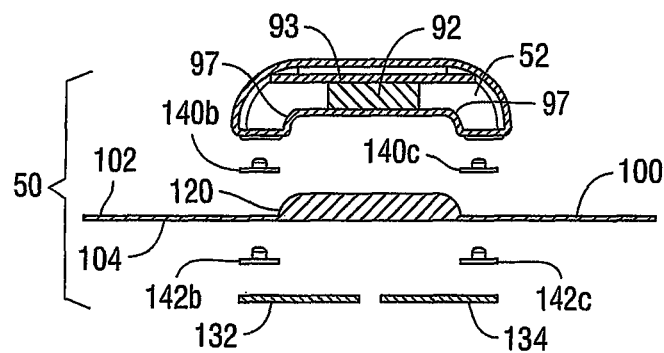
FIG. 16 is a sectional view of the wound care bandage prior to assembly taken along cut line A-A of FIG. 15.
Figure 17:
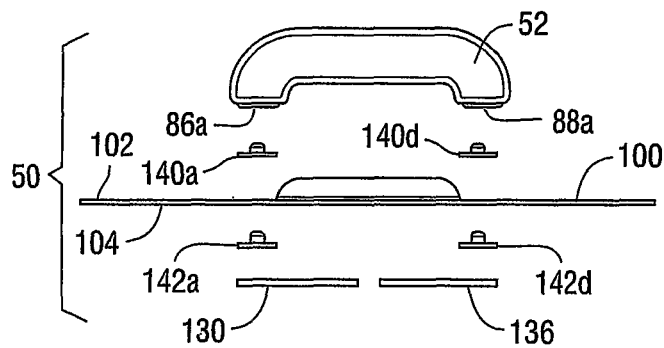
FIG. 17 is a side view of the wound care bandage prior to assembly.

FIG. 12 is a front view of the wound care bandage 50, FIG. 13 is a right side view of the wound care bandage 50, and FIG. 14 is a left side view of the wound care bandage 50. FIG. 15 is a top view of the would care bandage, and FIG. 16 is a sectional view taken along line A-A of FIG. 16 and that further details assembly of the wound care bandage 50, and FIG. 17 is another view of assembly of the wound care bandage 50.

Figure 19A:
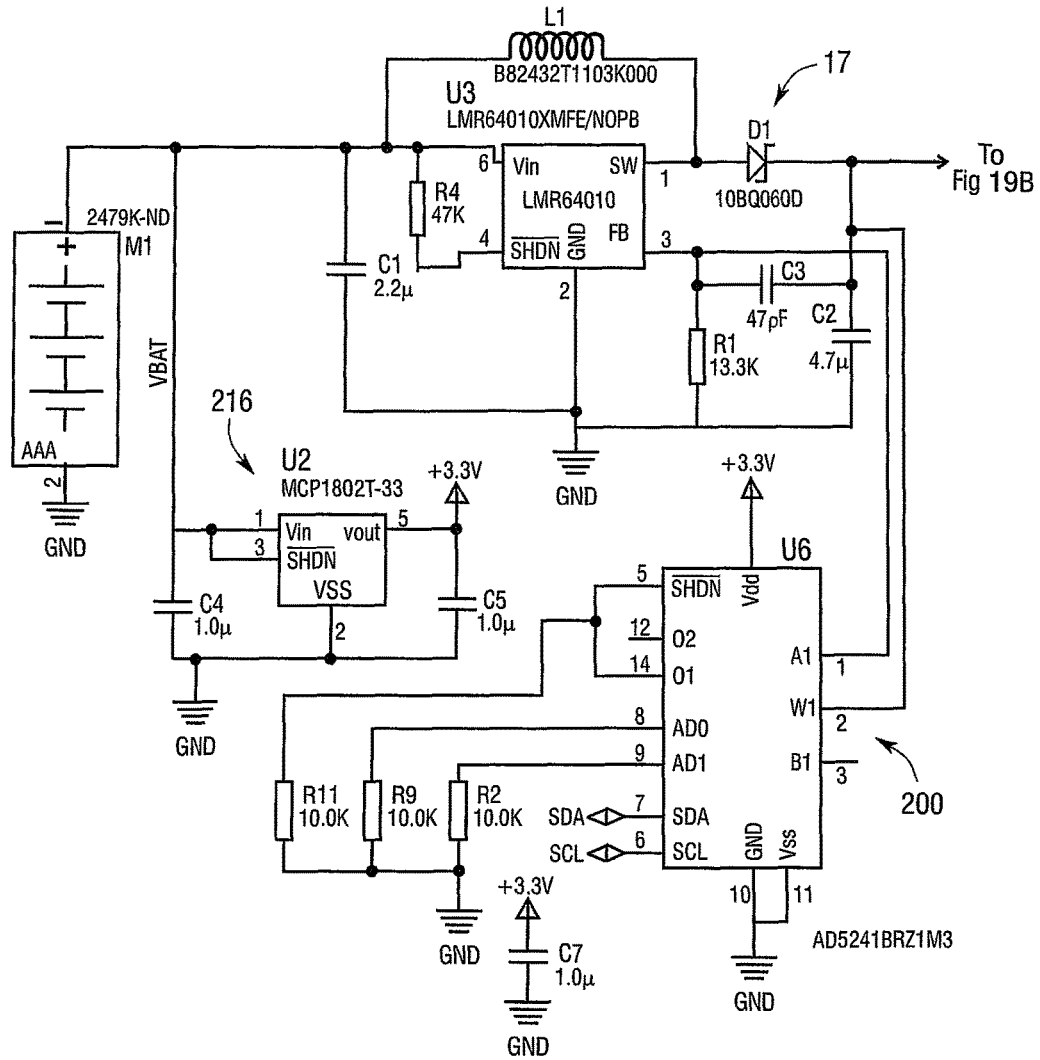
FIG. 19A is a schematic of a portion of the wound care bandage electronics utilized in the wound care bandage and continues onto FIG. 19B.
Figure 19A:
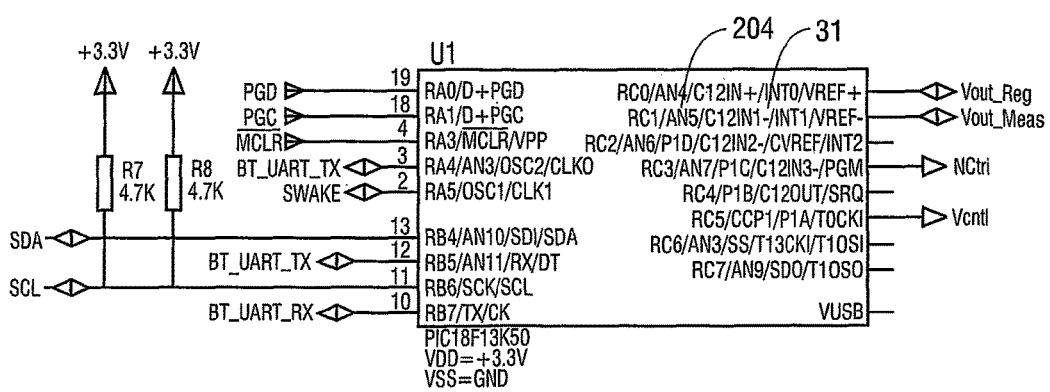
Figure 19B:
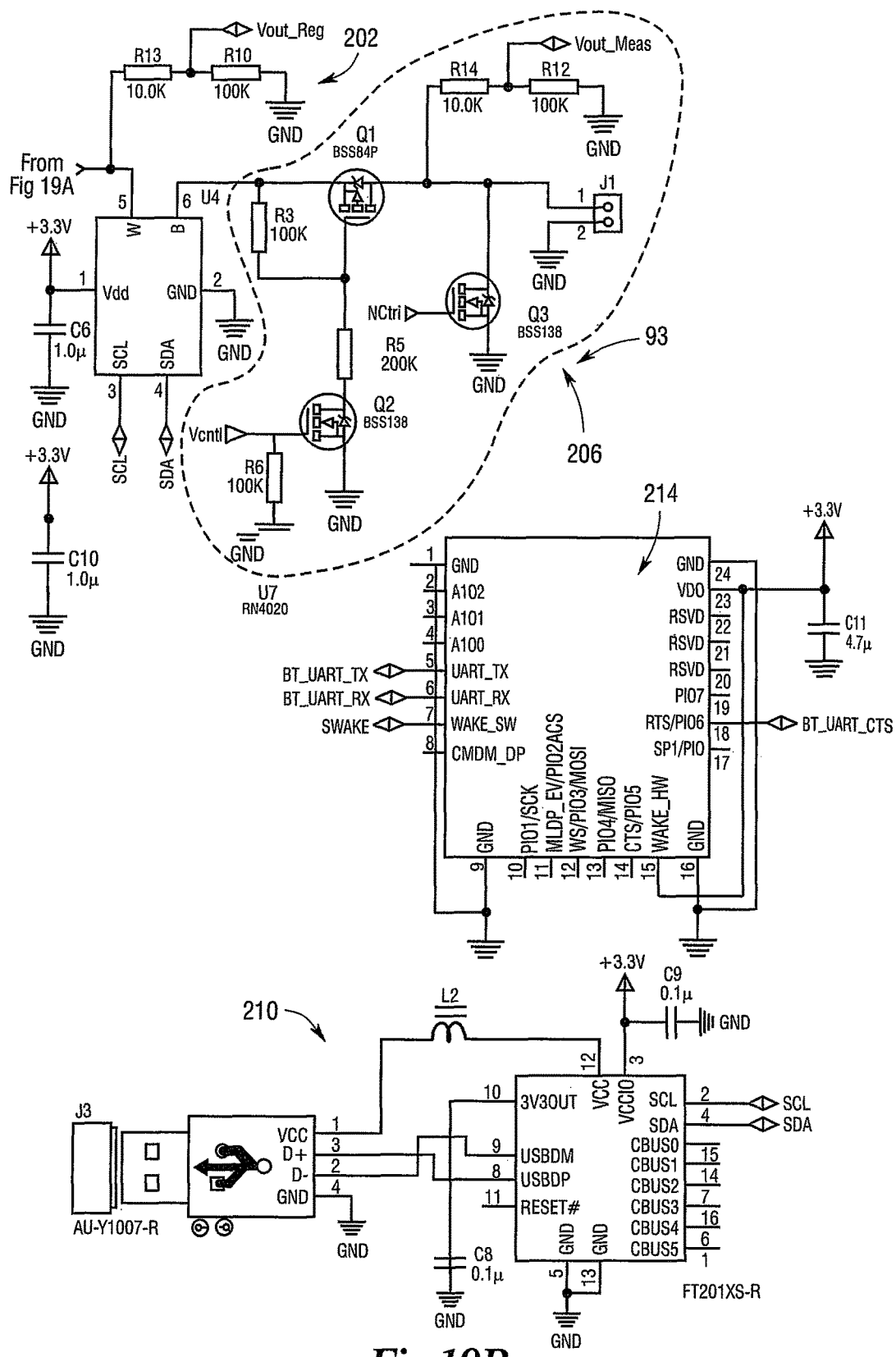
FIG. 19B is a schematic of a portion of the wound care bandage electronics utilized in the wound care bandage and continues from FIG. 19A.
Figure 21:
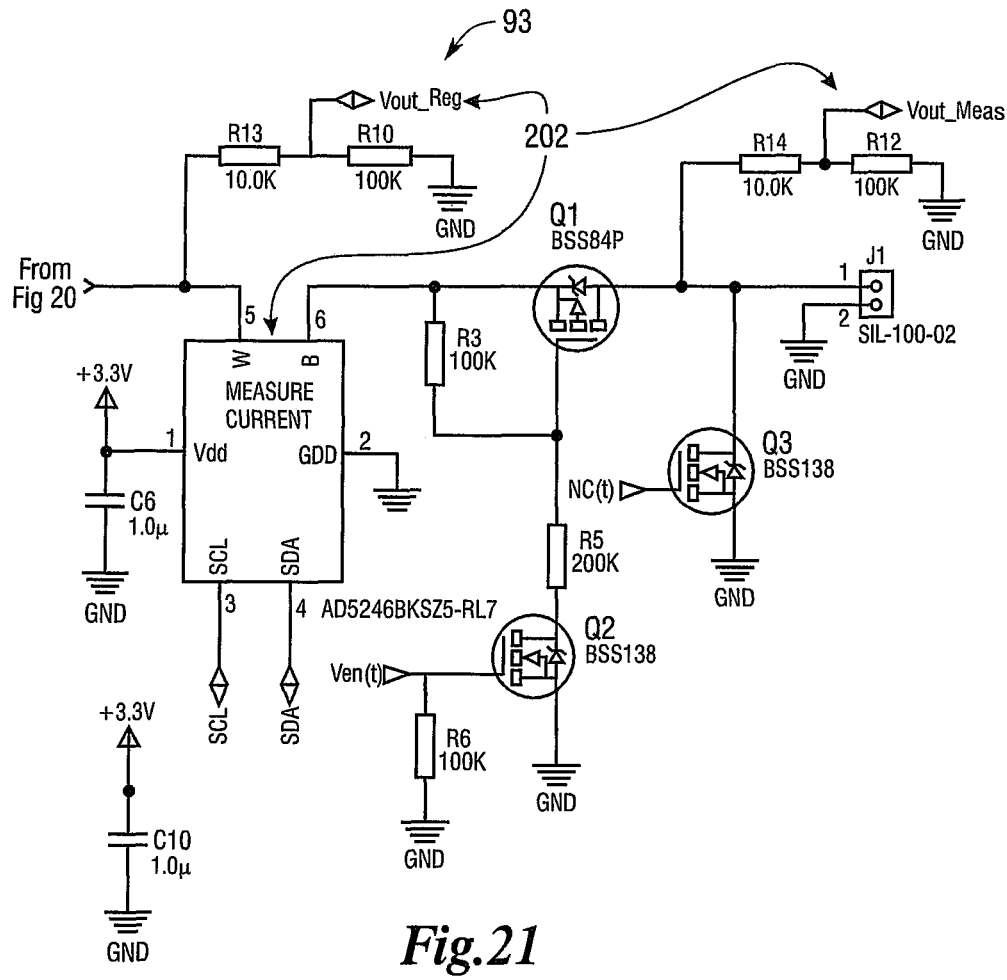
FIG. 21 is an expanded portion of FIG. 19B that is a continuation of the expanded portion shown in FIG. 20.

The electronics 93 are wired to the first and second conductive female snap components 86a, 86b, and the third and fourth conductive female snap components 88a, 88b to control the flow of current to the each of the first, second, third and fourth snap button electrodes 147a, 147b, 147c and 147d. The wound care MCU 31 does not interface directly with the first, second, third and fourth snap button electrodes 147a, 147b, 147c and 147d as shown in FIGS. 19A and 19B and 21, wherein J1 is a connector that is embodied as a wire connection to the first, second, third and fourth snap button electrodes 147a, 147b, 147c and 147d.

Each of the second strip sides 130b, 132b, 134b and 136b of the first, second, third and fourth electrically conductive adhesive strips 130, 132, 134 and 136 is moved into contact with the skin 55 of a patient 53 and adhered to the skin 55 such that they surround the wound 51, while at the same time each of the first, second, third and fourth snap button electrodes 147a, 147b, 147c and 147d contact the skin 55 of the patient 53 such that electrical current can flow across the wound 51. In addition, after the wound care bandage 50 is adhered to the skin 55 of the patient 53, the patient 53 can freely move and is not tethered to cords or other medical devices, because the wound care bandage 50 is a self-contained treatment bandage. In addition, health care providers can easily use the wound care bandage 50 and the administration process is simplified for trained personnel.

In addition, use of the wound care bandage 50 reduces costs. In particular, the electronics housing 52 and the wound care bandage electronics 93 disposed therein can be removed, cleaned, and reused by pulling the first and second conductive central snap components 140a, 140b, respectively, out of the first and second conductive female snap components 86a, 86b, and pulling the third and fourth conductive central snap components 140c, 140d, respectively, out of the third and fourth conductive female snap components 88a, 88b. The detached portion of the wound care bandage 50 can be disposed of replaced with new components, for example a new bandage layer 100 and pad 120, and new conductive central and base male snap components if desired.

Snap Button Electrodes Placement

It is pointed out that a minimum of two electrodes are called for that contact the skin 55 of the patient 53 in order for current to flow across the wound 51. The two electrodes are placed or arranged such that the wound 51 is located in a electrical current flow path that flows across the wound 51. Two electrodes will work as long as they are properly placed on the skin 55 on opposite sides of the wound 51. Improper electrode placement will result in the current flowing around the wound 51 resulting in the wound receiving little or no treatment whatsoever, and thus result in ineffective wound treatments.

In order to provide an improved treatment wherein the risk of current flowing around the wound 51 is decreased, the wound care bandage 50 has first, second, third and fourth snap button electrodes 147a, 147b, 147c and 147d as shown in FIG. 11, and in other preferred embodiments three of the first, second, third and fourth snap button electrodes 147a, 147b, 147c and 147d electrodes may be used, each being spaced from one another and surrounding the wound 51. In another preferred embodiment only two of the snap button electrodes are used, as they will provide current flow across the wound 51. For example, the first and second snap button electrodes 147a, 147b are utilized and can be properly placed such that current flows across the wound 51. In a three electrode embodiment only the first, second, third snap button electrodes 147a, 147b, 147c may be present.

The electronics 93 operates in a manner that allows for the multiplexing of each first, second, third and fourth electrically conductive adhesive strips 130, 132, 134 and 136 polarity so that any one these electrodes is capable of being a cathode, anode, or high impedance. By using a minimum of 3 of the first, second, third and fourth snap button electrodes 147a, 147b, 147c and 147d, no matter how these electrodes are placed, there will always be at least one combination of electrode polarities that causes current to flow through the wound 51, regardless of orientation of the electrodes to the wound. However, the use of all four of the first, second, third and fourth snap button electrodes 147a, 147b, 147c and 147d will provide an improved result because there are typically two combinations of electrodes that cause current to flow through the wound 51.

The physician programs the wound care MCU 31. Once treatment parameter is inputted and saved, the wound care MCU 31 will then begin creating the electric field that follows the parameters set by the physician. In some embodiments the patient 53 may adjust the parameters within the limits pre-set by the physician. The wound care bandage 50 will then pulse for a certain time at a certain current and at a certain voltage depending on the injury 54. The pulsed voltage aids in healing the wound 54.

To further illustrate electrode placement, reference is now made to FIGS. 18A-18F that show possible electrode placement and current flow across the skin 55 and wound 51 of the patient 53. As previously described, the first, second, third and fourth snap button electrodes 147a, 147b, 147c and 147d need to contact the skin 55 of the patient 53, and it is this connection that allows current flow through the wound 51. The first, second, third and fourth snap button electrodes 147a, 147b, 147c and 147d do not have to have a fixed polarity and in this preferred embodiment, and each has three states as follows:
1) Positive;
2) Negative; and,
3) High Impedance which makes the electrode appear invisible by making it a much higher path of resistance and thus minimal current flows through it.

By changing the three states of first, second, third and fourth snap button electrodes 147a, 147b, 147c and 147d there is a multitude of combinations. Since the wound care signal is a pulsed signal, in between each pulses, the polarities of the first, second, third and fourth snap button electrodes 147a, 147b, 147c and 147d shift before the next pulse continues. Therefore there exists at least a single pulse that occurs across the wound 51 within one cycle of pulsing.

Figure 18A:
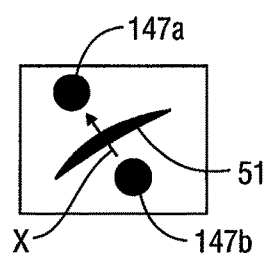
FIGS. 18A-18F are drawings detailing different electrode placement configurations relative to wounds.
Figure 18C:
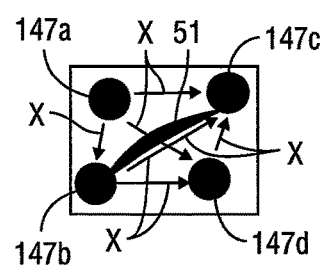
Figure 18E:
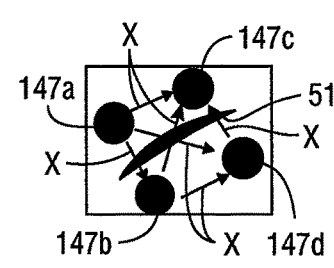
Figure 18B:
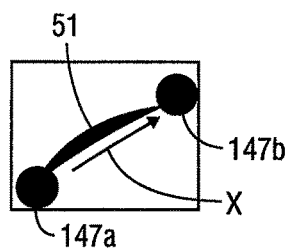
Figure 18D:
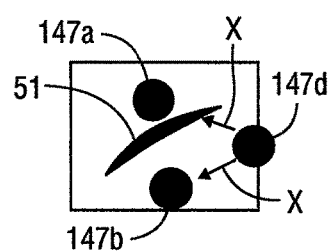
Figure 18F:
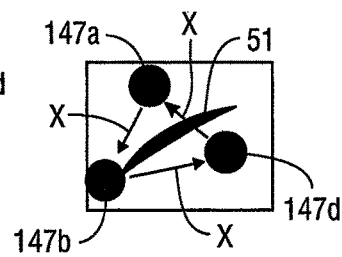

In FIGS. 18A-18F, electrodes are indicated by black filled circles, black arches indicate wounds 51, and current flow is indicated by the arrows designated X. In addition, the other parts of the wound care bandage 50 shown in FIG. 11 are not shown for the sake of clarity. Rather, all that is shown are various embodiments of the wound care bandage 50 depicting different numbers of first, second, third and fourth snap button electrodes 147a, 147b, 147c and 147d used, and placement of the various embodiments around the wound 51. That is, these embodiments depict various arrangements of the wound care bandage 50 when it is placed over the wound 51 and makes contact with the skin 55 of the patient 53. FIG. 18A depicts an embodiment wherein just the first and second snap button electrodes 147a, 147b are properly situated relative to the wound 51. The current the current flow path indicated by the arrow designated X will flow through and across the wound 51. However, in FIG. 18B, the placement of the first and second snap button electrodes 147a and 147b shows that the current flow path X bypasses the wound 51, and thus no or a minimal amount of treatment is provided to the wound 51. Thus, the possibility of non-treatment exists with the use of just two electrodes and extra care must be taken to ensure proper electrode placement. As shown in FIGS. 18C and 18D, there three electrode embodiments wherein three snap button electrodes provided 147a, 147b, 147d, and 147a, 147b, and 147a, respectively. Here each arrangement provides for at least one current flow path indicated by the arrows X to flow through the wound 51, and here illustrates an ideal placement of the snap button electrodes. FIGS. 18E and 18F show another preferred embodiment wherein the first, second, third and fourth snap button electrodes 147a, 147b, 147c and 147d are present and current flow paths indicated by the arrows designated X pass through the wound. In FIGS. 18E and 18F it is pointed out that it is a virtual certainty that the current will flow across the wound 51 and deliver treatment to the wound each cycle. FIGS. 18E and 18F show that even in a worst case placement of the first, second, third and fourth snap button electrodes 147a, 147b, 147c and 147d relative to the wound 51, current will still flow across the wound 51 and thus provided treatment to the wound 51.

In other preferred embodiments there may be additional snap button electrodes, for example fifth and sixth snap button electrodes or more (not shown) that would ensure even more combinations that lead to current flowing across the wound. Such embodiments will add to the weight and complexity of the wound care bandage 50.

The battery 92 is rechargeable as previously mentioned and the wound care bandage electronics 93 are small and disposed in the electronics housing 52, and this makes the wound care bandage 50 lightweight. In another preferred embodiment, the battery 92 is capable of being re-charged. Additionally, in another preferred embodiment, the electronics can be designed such that energy can be received wirelessly. Due to the power requirements, it in this preferred embodiment Radio Frequency (RF), Magnetic Induction, or highly resonance induction technologies can be used to power the electronics wirelessly.

Wound Care Bandage Electronics

Turning now to FIGS. 1-4 and FIGS. 19A and 19B-24, FIGS. 19A and 19B show the wound care bandage electronics 93 in a single figure. FIGS. 20-24 are expanded views of portions of FIGS. 19A and 19B, such that together FIGS. 20-24 show all that is shown in FIGS. 19A and 19B. It is pointed out and it is to be understood that some of the components shown in FIGS. 19A and 19B are used in connection with each of the first, second, third and fourth snap button electrodes 147a, 147b, 147c, 147d, and they are need to be replicated for each of the first, second, third and fourth snap button electrodes 147a, 147b, 147c, 147d. But, for the sake of clarity, these components are only shown once in these drawing figures with it being understood that they are replicated for each of the first, second, third and fourth snap button electrodes 147a, 147b, 147c, 147d.

Figure 20:
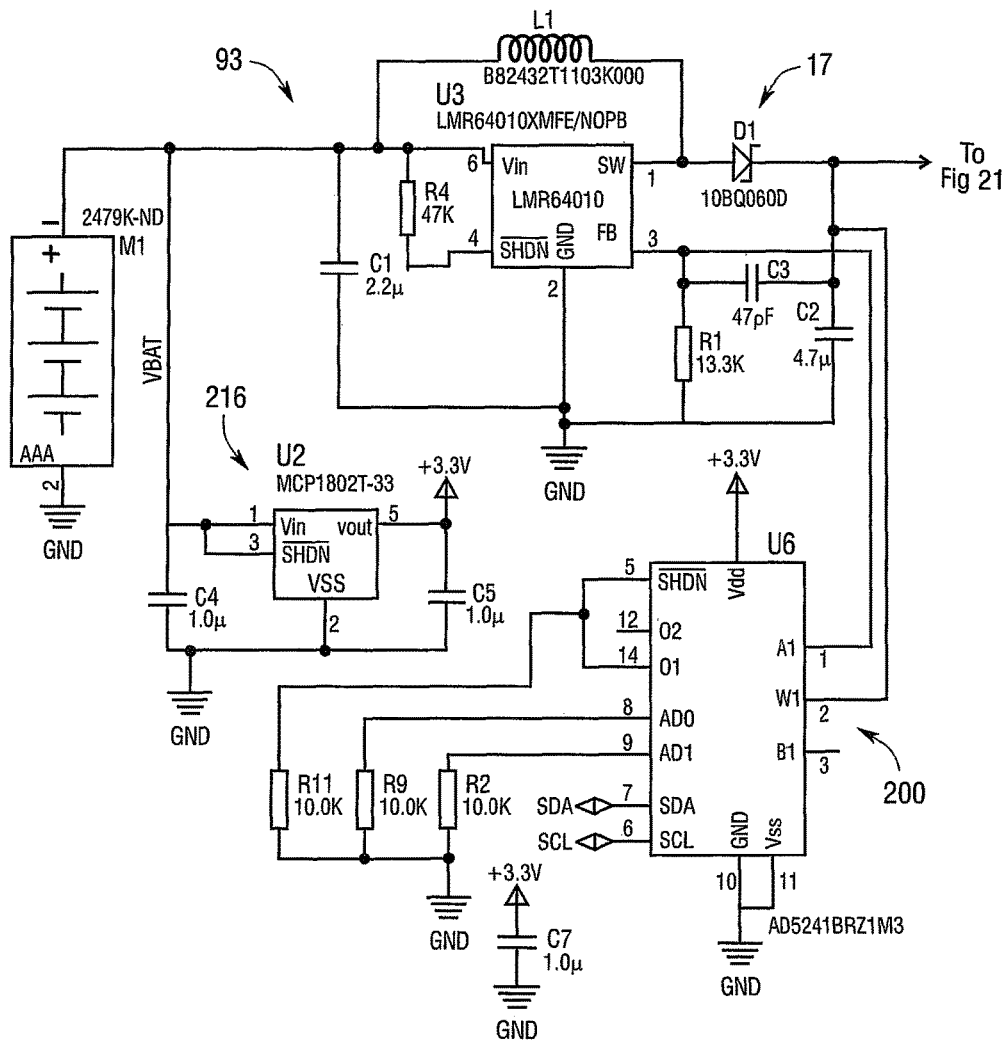
FIG. 20 is an expanded portion of FIG. 19A that continues onto FIG. 21.

The system regulator 17 is set to be at or above the maximum voltage that is required, and for purposes of the wound care bandage 50 the high voltage is about 40V. The system regulator 17 boosts the voltage from the battery to the higher voltage. This is accomplished by use of a standard switching boost topology that consists of a switch, which opens and closes, an inductor and capacitor bank. This is show in the circuit diagram shown in FIGS. 19A and 19B and 20. In one of the preferred embodiments as shown, the system regulator is a LMR64010 regulator. LMR64010 regulators are commercially available from Texas Instruments, Dallas, Tex. and the use and operation of boost regulators is well known to those having ordinary skill in the art. In FIG. 20 it is pointed out that C3, C2 and R1 make up the compensation network for the LMR64010. In addition, R4 ensures the system regulator 17 remains enabled when power is applied. In one preferred embodiment the wound care bandage electronics 93 may shutdown when the input voltage drops to a predetermined level, and this could be done through a Zener diode or by adding a resistor from the shutdown pin to ground such that the ratio of R4 to the new resistor would create a resistor divider.

As shown in FIG. 20, there is the power control circuit 200 portion of wound care bandage electronics 93. It is pointed out that Since the LMR64010's output is fixed based on the feedback network, a digital potentiometer (U6) is provided in order to actively change the output voltage. In this embodiment the U6 is connected to the wound care MCU 31 such that the wound care MCU 31 will send a command using a I2C interface in order to change the value of U6.

As shown in FIG. 21, voltage measuring circuitry 202 is shown. It is pointed out that safety mechanisms are built into the power supply block as well as some signals fed back to the wound care MCU 31. Current is measured on the output side of the current so as to ensure current flow does not exceed a predetermined safe level. As shown in FIG. 19B in dashed line and again in FIG. 22, the voltage measuring circuitry 202 is repeated for each of the first, second, third and fourth snap button electrodes 147a, 147b, 147c, and 147d. For the sake of clarity the voltage measuring circuitry 202 is only shown once in the drawing figures with the understanding it is repeated for each of the first, second, third and fourth snap button electrodes 147a, 147b, 147c, and 147d. In the case in which the signals are sent back to the wound care MCU 31, wound care software 33 will disable the wound care bandage 50 the wound care software 204 (FIG. 24) sense that the battery voltage is has dropped below a predetermined level of, for example 2V. Programming a microcontroller such as the wound care MCU 31 is well known to those having ordinary skill in the art and thus not described in greater detail herein. Additionally, it is there a first layer of protection for ensuring that the first, second, third and fourth snap button electrodes 147a, 147b, 147c and 147d are in fact in contact with skin 55 of the patient 53, and not through a short like metal or each other. This ensures the wound care bandage 50 does not damage itself by running at load through a low resistive path. Additionally since a short circuit might damage components faster than the wound care MCU 31 can respond, additional components such as an operational amplifier can be used to detect the change in voltage as fast as a few microseconds. This speed can be very useful to ensure that power is reduced or cut off if a safety condition were to occur. To maintain normal operation, as shown in FIGS. 21, R13, R10 and R14, R12 form a resistive divider with each of the respective groups. This divider ensures that the voltage does not exceed the maximum voltage that the AD pin of the wound care MCU 31 can accommodate.

As shown in FIGS. 1, 2 and 21, there is current control circuitry 206 for the wound care signal conditioner 21, and the wound care signal conditioner 21 is under the control of the wound care MCU 31. The wound care signal conditioner 21 converts the power received from wound care regulator 19 into a preprogrammed waveform. This includes but not limited to creating the pulse duration, converting the voltage to the proper level, modulating the signal, and creating signals needed to support the treatments of patients 53. As shown, the wound care signal conditioner 21 includes switches that turn the output on and off, and contain a feedback network, shown in FIG. 21, used to ensure that current isn't being exceed. If the current is exceed than the voltage is reduced until the current is within a safe or programmed limit. Additionally, current control circuitry 206 for the wound care signal conditioner 21 controls the rise and fall times of the waveform to ensure they meet the requirements of a pre-programmed levels determined by a treating doctor.

As shown in FIG. 21, the digital potentiometer U4, which is used to limit the current on the output. U4 is controlled by the wound care MCU 31 through I2C. Q1 is a power path field-effect transistor (FET) that acts as a switch to connect and disconnect the electrode output (the output of the first, second, third and fourth snap button electrodes 147a, 147b, 147c and 147d) from the positive power rail. It is through this FET (Q1) that the voltage is turned on and off in pattern that matches the expected output signal. Additionally, Q3 may be closed if the electrode (the output of the first, second, third and fourth snap button electrodes 147a, 147b, 147c and 147d) is intended to be the negative connection for a given pulse. It is pointed out that if Q3 is closed when connecting the electrode output to GND, then Q1 must be open or the wound care regulator 19 would be connected through Q1 and Q3 to GND causing the wound care bandage 50 to not operate properly. By closing Q1, the voltage is connected to the output connector J1. When Q1 is open, the voltage is no longer connected. By adjusting this on and off time, pulses can be created. Q1 is controlled by the wound care MCU 31 through Q2. Since Q1 is in the power path a P-channel FET is used so that additional boost regulators would not be needed to activate Q1. Q2 is an N-channel FET that will ground gate of Q1 in order for the Q1 gate voltage to be sufficient for the FET to close. Since the voltage of Q1 is about 30V, R5 is provided so that the voltage at the gate does not equal zero when the wound care regulator 19 is at 40V. R3 is a pull up resistor responsible for turning off Q1, and forms a resistor divider with R5 when Q2 is closed. When Q2 is open, R5 is no longer connected to ground and R3 then pulls the gate of Q1 up to the source voltage and thus causes Q1 to open. The gate of Q2 is connected to the wound care MCU 31 and its voltage threshold is lower than the minimum logic 1 voltage for the wound care MCU in order for this switch to activate. Since the source of Q2 is connected to ground, then the voltage on the gate only needs to be at the threshold voltage in order for the FET to close. To achieve a high-impedance connection for an electrode and thus minimizing the current flow through the particular electrode (here one of the first, second, third and fourth snap button electrodes 147a, 147b, 147c and 147d), both Q1 and Q3 must be open. Neither Q1 nor Q3 are ever completely open as they would be in an ideal diode, they are considered to be high impedance.

It is further pointed out that for each electrode in the system (the first, second, third and fourth snap button electrodes 147a, 147b, 147c and 147d), there is an additional output. The block diagram and the circuits shown and discussed in FIG. 21 are duplicated for each electrode (not shown for the sake of clarity). Additionally, it is to be understood that the wound care MCU 31 shown in FIGS. 19A, 19B and 24 will require additional I/O pins connected to the extra circuitry (not shown for the sake of clarity).

The filter 27 shown in FIGS. 1 and 2 are set such that power from the wound care signal conditioner 21 returns through the wound care electrodes (here the first, second, third and fourth snap button electrodes 147a, 147b, 147c and 147d. It is pointed out that the wound care signal conditioner 21 produces a signal that is modulated to match the frequency of the filter 27. The filter 27 blocks all the signals that don't match its frequency thus only the intended signal gets through. In other preferred embodiments, the filter 27 is not necessary.

As shown in FIGS. 1, 3, FIGS. 19A and 19B and 24 there is the wound care MCU 31 that includes the main processor for the system. The wound care MCU 31 is responsible for managing the system in terms of making sure there is adequate power, as well as controlling the wound care signal conditioner 21 such that the output treatment matches what is programmed in the wound care microcontroller database 33. The wound care MCU 31 also has a wound care processor 35, a wound care memory component 37 and stores wound care software programs 39. Thus, the wound care MCU 31 stores the wound care software programs 39, manages the user interface 27 utilized by the physician or other users, and executes the pre-programmed wound care software programs 39 as needed. The wound care MCU 31 also ensures the system is running safely and to detect any anomalies from the outside. Additionally the wound care MCU 31 can be connected to a wireless transceiver and report the system data to another device, server, and the like. If the wound care MCU 31 determines that any portion of the wound care bandage 50 is running outside of its expected use case, then the wound care MCU 31 will turn off and disable the wound care bandage 50. The wound care MCU 31 is designed to run at slow speeds in order to minimize power consumption. There is a minimum frequency at which the wound care MCU 31 needs to operate, in particular, wound care MCU 31 is unable to control waveforms that are faster than the maximum frequency of the wound care MCU's 31 system clock speed. Thus, the wound care MCU 31 waveform should be the same or greater than the maximum frequency wound care bandage 50 can be programmed with.

Figure 23:
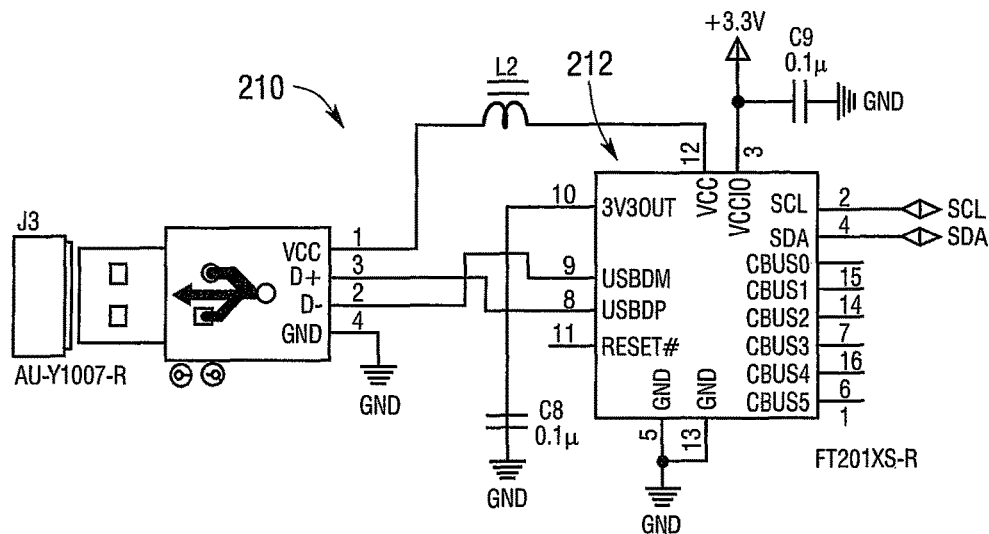
Figure 24:
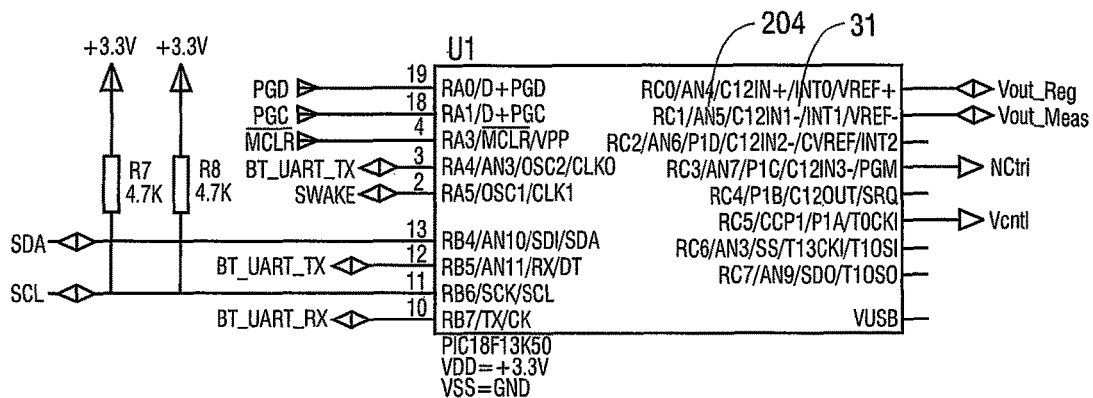

As shown in FIGS. 19A and 19B and 24, R7 and R8 act as pull up resistors for the I2C lines and it is these are the lines that allow U1 to communicate with the two digital potentiometers as well as an input from a universal serial bus (USB) 210 shown in FIG. 23. Additionally pins 15 and 16 of the wound care MCU 31 are the A/D inputs for reading the output voltage. Vcntl indicated on pin 5 is the output to Q2 that is used to generate the pulse wave. This pin is also a pulse width modulation (PWM) pin as the wound care MCU 31 can create the pulse shapes directly.

As shown in FIGS. 19A and 19B and 23, the USB 210 may be used as a quick way to adjust the output pulse shapes. There is a USB transceiver 121 and supporting connectors and components. USB is well known to those having ordinary skill in the art and therefore not described in greater detail herein. In the alternative embodiment the USB 210 is replaced with an RF transceiver. The USB transceiver 213 (and RF transceiver) connect to the wound care MCU 31 using a SPI bus, UART/USART, I2C, or some other communications bus well known to those having ordinary skill in the art.

Figure 22:
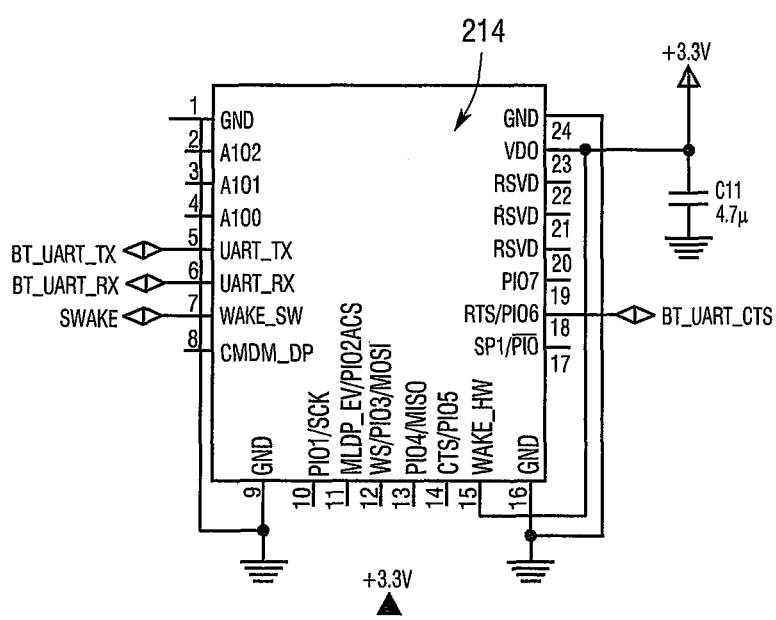
FIGS. 22-24 are expanded views of portions of FIGS. 19A and 19B.

As shown in FIGS. 19A and 19B and 22, an additional control and reporting circuit block is the RF transceiver 214. In one of the preferred embodiments Bluetooth wireless technology is used and is currently available Smartphones that contain Bluetooth technology and other portable mobile devices that contain Bluetooth technology. The use of Bluetooth allows for real-time information exchange between the electronics and the phone. The transceivers communications requirements will vary and need to be compatible with the communications protocol supported by the wound care MCU shown in FIGS. 19A and 19B and 24. In this way, the communications to and from the RF transceiver can be controlled by the wound care MCU 31.

As shown in FIGS. 1, 4 and 20, there is there is shown the supportive powering system 216. It is pointed out that the wound care MCU 31 electronics need a low power signal in order to operate properly, this power system is set to simply deliver the power needed for the system to function. It is pointed out that this is different than the main power path shown in FIG. 2 wherein the power flows to wound care regulator 19 and then and ultimately to the electrodes (here the first, second, third and fourth snap button electrodes 147a, 147b, 147c and 147d). The supportive powering system 216 is used for the controlling and managing of the wound care signal conditioner 21 as well as the user interface 29 shown in FIG. 1.

U2 is a regulator used to regulate the voltage from the input to a voltage that is acceptable by the wound care MCU 31, for example 3.3V. The wound care signal conditioner 21 and the filters 27 may require more power or different voltages, other than 3.3V, thus other regulators can be added as required.

Wireless Telemetry

Thus, as described above, wireless telemetry is provided for herein. For example, and because no two wounds and no two patients are the same, the electronics described herein are customizable by the physician. This feature also allows for logging of treatment and other capabilities that may or may not be tied specifically to the treatment. Telemetry eliminates the need for the health care provider to directly tether to the wound care bandage 50, and this allows the patient 53 to be mobile while wearing and receiving treatment via the health care bandage 50. Again, wired connections can cause problems, because the cords can cause pressure on the wound 51 caused from the added weight of cords pulling on the electronics. Use of wireless technology as described herein solves this tethering problem because no cords are required.

It is pointed out that every wound 51 is different so the parameters need to be adjusted in accordance with each wound 51. The physician programs the device and the parameters are saved to the wound care MCU 31. Once saved, the wound care MCU 31 will then begin creating the electric field that follows the parameters set by the physician, while the patient may adjust the parameters within the limits pre-set by the physician. The pulses will pulse for a certain time at a certain current and at a certain voltage depending on the wound 51.

Figure 25:
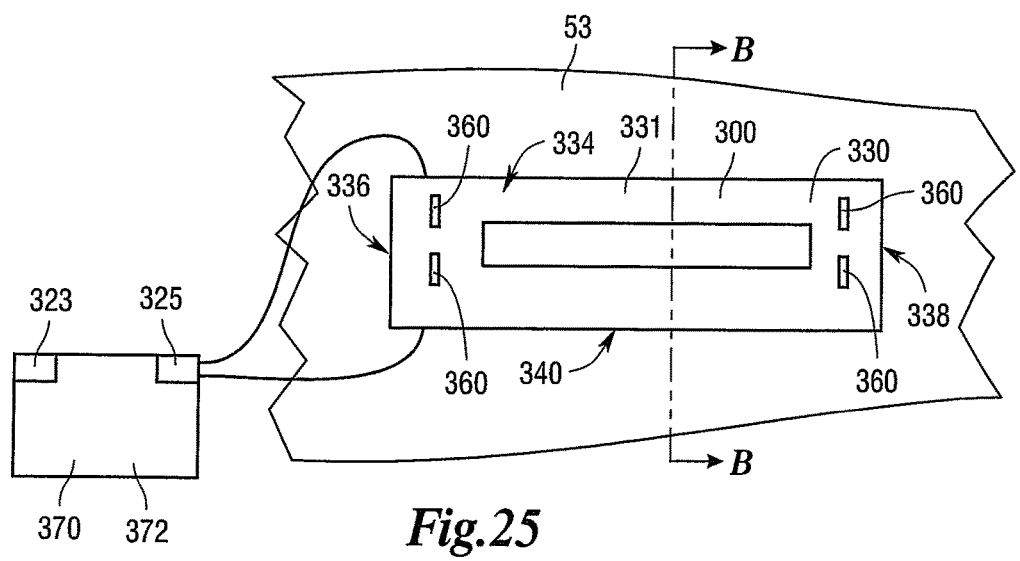
FIG. 25 is a top plan view of another preferred embodiment showing a high profile bandage.
Figure 26:
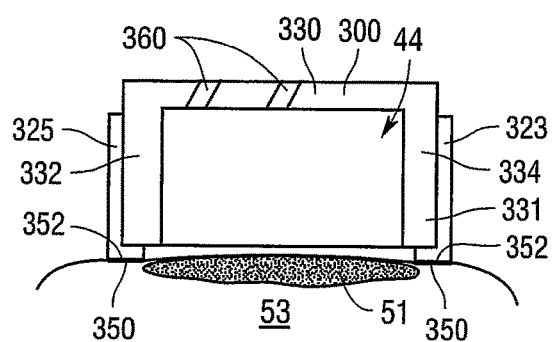
FIG. 26 is a sectional view of the high profile bandage taken along line B-B of FIG. 25.

In another preferred embodiment as shown in FIGS. 25 and 26, the wound healing system 10 includes a high profile bandage 300. The high profile bandage 300 has opposed first and second sides 332, 334, opposed ends 336, 338, and opposed base and cover sides 340, 342. As shown in the sectional view of FIG. 26 take along line B-B of FIG. 25, the high profile bandage 300 hollow to allow air to access the wound 51. An adhesive 350 that coats the bandage edges 352 such that the high profile bandage 300 can be adhered to the patient 53 and keep out debris and allow for air transfer to the wound 51.

The bandage 300 is made from antimicrobial fabric in one of the preferred embodiments. High profile bandage 300 is also made of a conductive fabric 331 having, for example copper wires, woven into its structure. The size and shape of the high profile bandage 300 may be patient specific to the particular injury suffered, and may be circular, rectangular or square, or any suitable shape, and may be custom built or pre-sized. In other preferred embodiments the high profile bandage 300 may be made of foam of foam padding.

There are negative metal plate electrode 323 is joined to the first side 332 of the high profile bandage 300, and the positive metal electrode plate 325 is joined to the second side 334 of the high profile bandage 300. When current is applied the combination of the current flowing through the high profile bandage 300 and thus the wound 51, and the natural aeration and oxygenation of the wound 51 due to construction of the bandage result in the wound 51 healing. As shown, there is a battery pack 370 and electronic pulse controller 372 wired to the first and second electrodes 323, 325 to supply power to the electrodes 323, 325 and the conductive fabric 331.

The high profile bandage 330 also defines airflow channels 360 for aeration in one of the preferred embodiments.

It will be appreciated by those skilled in the art that while the wound care bandage 50 and high profile bandage 330 have been described in detail herein, the wound care bandage 50 and high profile bandage 330 are not necessarily so limited and other examples, embodiments, uses, modifications, and departures from the embodiments, examples, uses, and modifications may be made to the wound care bandage 50 and the high profile bandage 33 without departing from the process and all such embodiments are intended to be within the scope and spirit of the appended claims.

What is claimed:

1. A wound care bandage for treating a wound, the wound care bandage comprising:
   a bandage layer that defines a pad recess and a pad and the pad is disposed in the pad recess;
   a first snap button electrode and a second snap button electrode wherein each of the first snap button electrode and the second snap button electrode extends through the bandage layer and the bandage layer is secured to the first snap button electrode and the second snap button electrode;
   an electronics housing secured to the first snap button electrode and secured to the second snap button electrode and a battery and wound care bandage electronics disposed in the electronics housing and wired to the first and second snap button electrodes;
   wherein the battery is for powering the wound care bandage electronics and powering the first snap button electrode and the second snap button electrode such that the first and second electrodes are capable of delivering current to a wound; and,
   further wherein the wound care bandage electronics has a main power path and electrical power from the battery is sent from the main power path to a wound care regulator, then to a wound care signal conditioner, then to a filter, and from the filter to the first and second snap button electrodes.

2. The wound care bandage according to claim 1 wherein current paths exist between the first and second snap button electrodes and wherein the first and second snap button electrodes are disposed such that the wound is disposed between the first and second snap button electrodes such that electrical currents can flow through the wound when the first and second snap button electrodes are powered.

3. The wound care bandage according to claim 2 wherein the wound care bandage electronics control electrical pulse cycles between the first and second snap button electrodes.

4. The wound care bandage according to claim 1 further including first and second conductive adhesive strips and each defines a strip opening and the bandage layer has opposed first and second bandage layer surfaces and the first and second conductive adhesive strips are adhered to the second bandage layer surface such that the first snap button electrode extends through the strip opening defined in the first conductive adhesive strip and the second snap button electrode extends through the opening strip opening defined in the second conductive adhesive strip.

5. The wound care bandage according to claim 1 wherein each of the first and second snap button electrode includes:
   a) a first conductive female snap component that is secured to the electronics housing;
   b) a first conductive central snap component having a male member and the male member defines a female recess and the male member is capable of being fitted in the female snap component; and,
   c) a first conductive base male snap component that has a base male member that is capable of being fitted in the female recess of the male member of the first conductive central snap component, such that the first conductive female snap component and the first conductive central snap component and the first conductive base male member are capable of being releasably snapped together to form the first snap button electrode.

6. The wound care bandage according to claim 1 wherein the pad and the bandage layer are made of antimicrobial material.

7. The wound care bandage according to claim 1 further including a third snap button electrode that extends through the bandage layer and the bandage layer is secured to the third snap button electrode, and further including a third conductive adhesive strip that defines a strip opening, and the bandage layer has opposed first and second bandage layer surfaces and the third conductive adhesive strip is adhered to the second bandage layer surface and the third snap button electrode extends through the strip opening defined in the third adhesive strip, and wherein the first, second, and third snap button electrodes are arranged in a triangular shape such that first, second, and third snap button electrodes can be positioned around a wound such that the wound is surrounded by the first, second and third snap button electrodes.

8. The wound care bandage according to claim 7 further including a fourth snap button electrode that extends through the bandage layer and the bandage layer is secured to the fourth snap button electrode, and further having a fourth conductive adhesive strip that defines a strip opening, and the fourth conductive adhesive strip is adhered to the second bandage layer surface such that the fourth snap button electrode extends through the strip opening defined in the third adhesive strip and wherein that the first, second, third and fourth snap button electrodes are arranged in a quadrilateral shape with each of the first, second, third and fourth snap button electrodes forming a corner of the quadrilateral shape and wherein the first, second, third and fourth snap button electrodes can be positioned to surround a wound such that electrical current can flow through the wound.

9. The wound care bandage according to claim 8 wherein each of the third and fourth snap button electrode includes:
   a) a first conductive female snap component that is secured to the electronics housing;
   b) a first conductive central snap component having a male member and the male member defines a female recess and the male member is capable of being fitted in the female snap component; and,
   c) a first conductive base male snap component that has a base male member that is capable of being fitted in the female recess of the male member of the first conductive central snap component, such that the first conductive female snap component and the first conductive central snap component and the first conductive base male member are capable of being releasably snapped together to form the first snap button electrode.

10. The wound care bandage according to claim 1 wherein the wound care bandage electronics have a supportive power path that includes the battery, a system regulator, a wound care microcontroller and a wound care signal conditioner such that electrical power from the battery is delivered to the system regulator and then microcontroller and the wound care signal conditioner.

11. The wound care bandage according to claim 10 further wherein the wound care bandage electronics include a RF transceiver to allow for real-time information exchange between the wound care bandage electronics and a portable mobile device.

12. The wound care bandage according to claim 1 wherein the electronics housing and the wound care bandage electronics disposed therein can be reused by detaching the wound care housing from the bandage layer such that a clean bandage layer and pad can be attached to the electronics housing.

13. A method for delivering current to wound, the method comprising the acts of:
providing a bandage layer that defines a pad recess and providing a pad and disposing the pad in the in the pad recess;
providing a first snap button electrode and a second snap button electrode and extending the first snap button electrode and the second snap button electrode through the bandage layer and securing the bandage layer to the first snap button electrode and second snap button electrode;
providing an electronics housing and securing the electronics housing to the first snap button electrode and the second snap button electrode, and providing a battery and wound care bandage electronics and disposing the battery and the wound care bandage electronics in the electronics housing such that the wound care bandage electronics can send electrical pulses to the wound;
providing the wound care bandage electronics with an RF transceiver and providing a portable mobile device and wirelessly controlling the output electric pulses generated by the wound care bandage electronics and wirelessly monitoring and adjusting the out electric pulses with the portable mobile device to allow for real-time information exchange and control between the wound care bandage electronics and the portable mobile device; and,
providing first and second conductive adhesive strips and each defines a strip opening and the bandage layer has opposed first and second bandage layer surfaces, and the first and second conductive adhesive strips are adhered to the second bandage layer surface such that the first snap button electrode extends through the strip opening defined in the first conductive adhesive strip and the second snap button electrode extends through the strip opening defined in the second conductive adhesive strip and adhering the first and second conductive strips on the skin and wherein the wound is disposed between the first and second snap button electrodes and the first and second snap button electrodes make contact with the skin, and sending pulsed electric current to the first and second snap button electrodes to treat the wound.

14. The method for delivering current to a wound according to claim 13 further comprising the acts of providing third and fourth snap button electrodes and providing third and fourth conductive adhesive strips and each defines a strip opening and the bandage layer and the conductive third and fourth conductive adhesive strips are adhered to the second bandage layer surface such that the third snap button electrode extends through the strip opening defined in the first adhesive strip and the fourth snap button electrode extends through the strip opening, and adhering the third and fourth conductive strips to the skin.

15. The method for delivering current to a wound according to claim 14 further comprising the act of positioning the first, second, third and fourth snap button electrodes on the skin such that the first, second, third and fourth snap button electrodes surround the wound and wherein the wound care bandage electronics send pulsed electric current to the first, second, third and fourth snap button electrodes to treat the wound.

16. A wound care bandage for treating a wound, the wound care bandage comprising:
a bandage layer that defines a pad recess and a pad and the pad is disposed in the pad recess;
a first snap button electrode and a second snap button electrode and a third snap button electrode wherein each of the first, second and third snap button electrodes extends through and the bandage layer and the bandage layer is secured to the first, second and third snap button electrodes;
an electronics housing secured to the first, second and third snap button electrodes and a battery and wound care bandage electronics disposed in the electronics housing and wired to the first, second and third snap button electrodes and the wound care bandage electronics has a main power path and electrical power from the battery is sent from the main power path to a wound care regulator, then to a wound care signal conditioner, then to a filter, and from the filter to the first, second and third snap button electrodes;
wherein the battery is for powering the wound care bandage electronics and powering the first, second and third snap button electrodes and the first, second and third snap button electrodes are capable of being positioned around the wound such that the first, second and third electrodes are capable of delivering current to the wound; and,
wherein the wound care bandage electronics include a RF transceiver to allow for real-time information exchange between the wound care bandage electronics and a portable mobile device such that output electric pulses generated by the wound care bandage electronics and delivered to the first, second and third snap button electrodes can be wirelessly monitored and adjusted.

17. The wound care bandage for treating a wound according to claim 16 further including:
first, second and third conductive adhesive strips and each defines a strip opening and the bandage layer has opposed first and second bandage layer surfaces and the first, second and third conductive adhesive strips are adhered to the second bandage layer surface such that the first snap button electrode extends through the strip opening defined in the first conductive adhesive strip and the second snap button electrode extends through the opening strip opening defined in the second conductive adhesive strip and the third snap button extends through the strip opening defined in the third conductive adhesive strip; and,
wherein the wound care bandage electronics are capable of multiplexing the polarity of each of the first, second and third conductive adhesive strips such that any of the first, second and third conductive adhesive strips can be an anode, a cathode or have high impedance.

* * * * *